United States Patent [19]

Fischer

[11] Patent Number: 5,327,907
[45] Date of Patent: Jul. 12, 1994

[54] BIOMECHANICAL MEASUREMENT TOOL

[76] Inventor: Peter Fischer, 230 Ashbury St., San Francisco, Calif. 94117

[21] Appl. No.: 984,026

[22] Filed: Dec. 1, 1992

[51] Int. Cl.⁵ .............................................. A61B 5/103
[52] U.S. Cl. .................................. 128/774; 33/558.01
[58] Field of Search ......................... 128/774, 781, 782; 33/511, 512, 558.01, 558.08, 558.2, 558.4

[56] References Cited

U.S. PATENT DOCUMENTS

| 4,097,997 | 7/1978 | Bjornson | 128/774 |
| 4,201,226 | 5/1980 | Phillips | 128/774 |
| 4,226,025 | 10/1980 | Wheeler | 33/512 |
| 4,972,602 | 11/1990 | Howes | 33/558.01 |
| 5,154,003 | 10/1992 | Moore | 33/558.01 |
| 5,156,161 | 10/1992 | Lollar | 128/774 |
| 5,156,162 | 10/1992 | Gerhardt | 128/781 |

FOREIGN PATENT DOCUMENTS 2125548 3/1984 United Kingdom ................. 128/774

Primary Examiner—Max Hindenburg
Attorney, Agent, or Firm—Townsend and Townsend

[57] ABSTRACT

A skeletal measurement device is disclosed in which concave arcuate calipers extend from a central housing containing a gear actuated dial scale. Upon expansion of the ends of the concave calipers away from one another in reaching and measuring skeletal points on a body therebetween, the gear actuated scale measures the distance between the caliper ends. Preferably, the arcuate calipers are extensible to at least first and second lengths. Accordingly, the connected gear actuated dial scale is provided with corresponding scales indicating the correspondingly changed distance of the extended arms. When the instrument is extended with its calipers measuring skeletal reference points, an attached inclinometer provides gravitational angular reference to the vertical. Dependent upon how the central housing must be disposed to enable the calipers to reach about the body being measured, this inclinometer is hinged along a hinge axis parallel to a line between the ends of the calipers to allow rapid measurement of distance and angle between skeletal points. Preferably, the measuring instrument is suspended by an adjustable cord from the neck of the measuring therapist to free his or her hands for palpation, data recording, safety of patient and movement of the measuring arms during rapid repeatable measurement. Provision is made for the attachment of palpation ends to the ends of the concave arcuate arms so that the skeletal points on a body can be palpated at the same time as the instrument is suspended around the therapist's neck and the measurements are read.

7 Claims, 7 Drawing Sheets

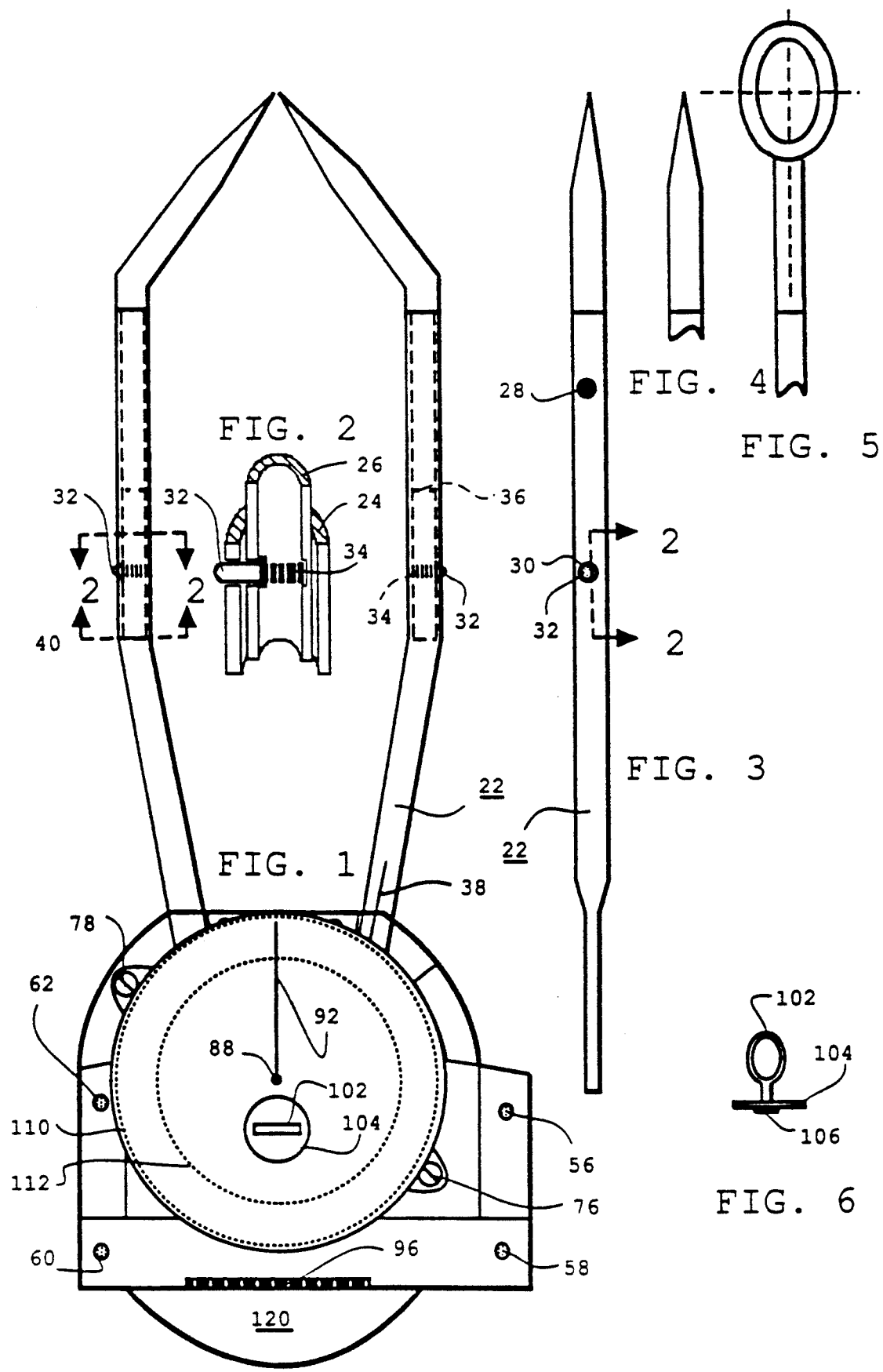

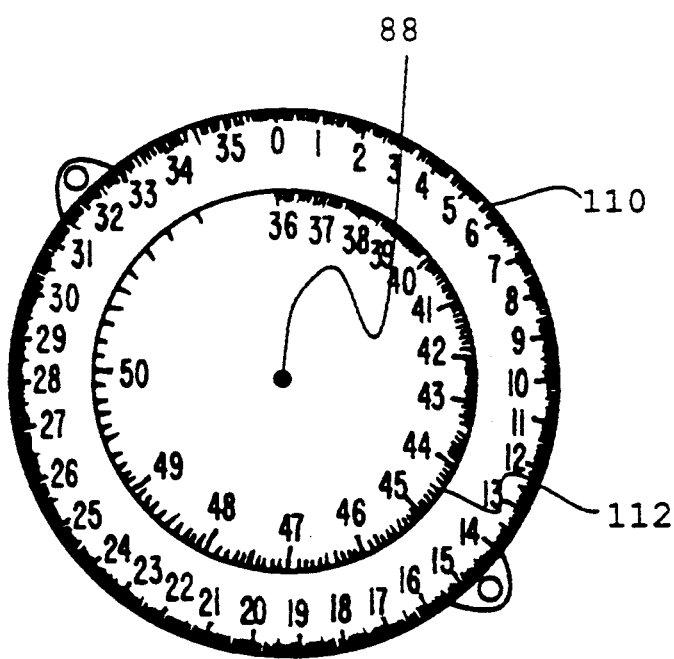
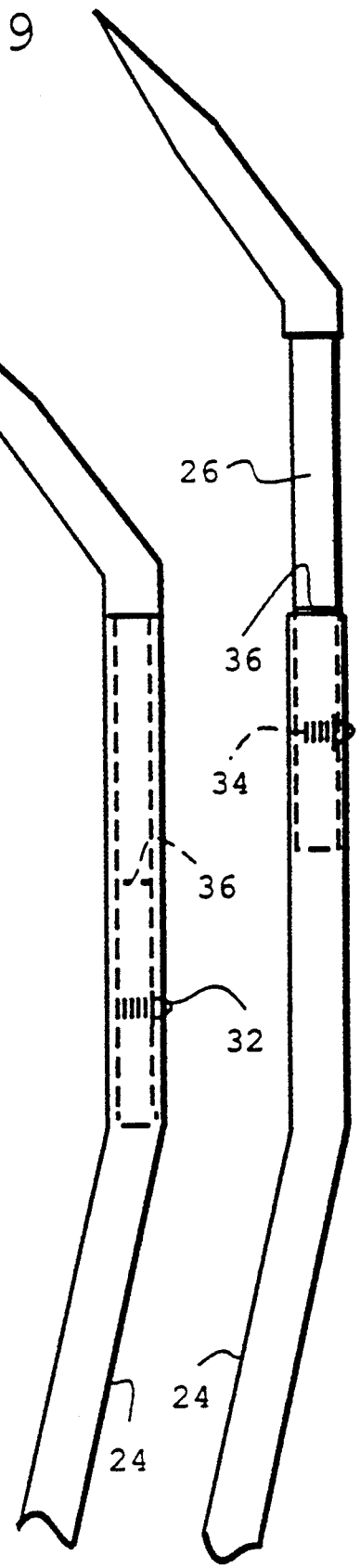

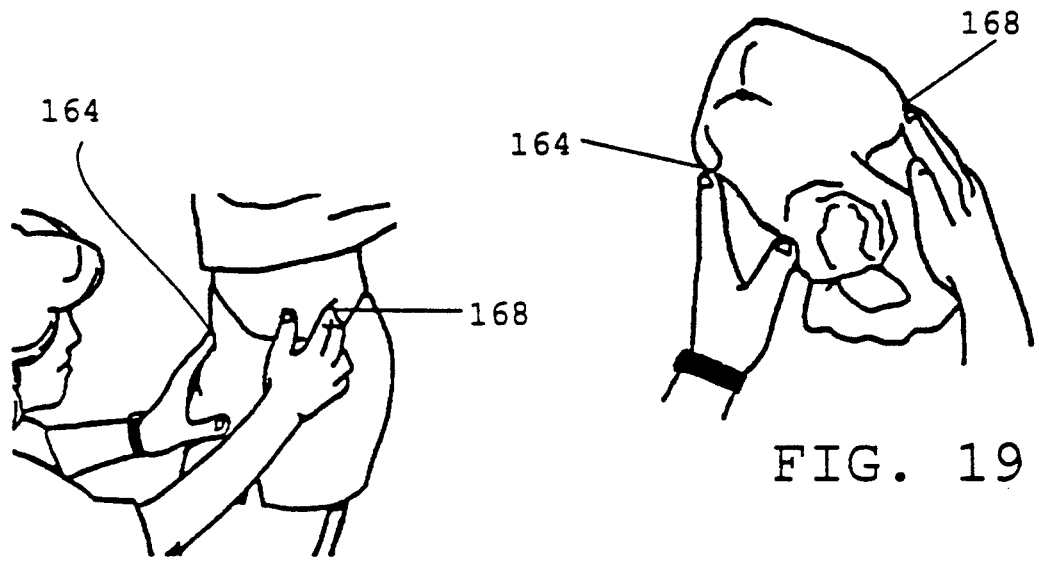
FIG. 18
FIG. 19
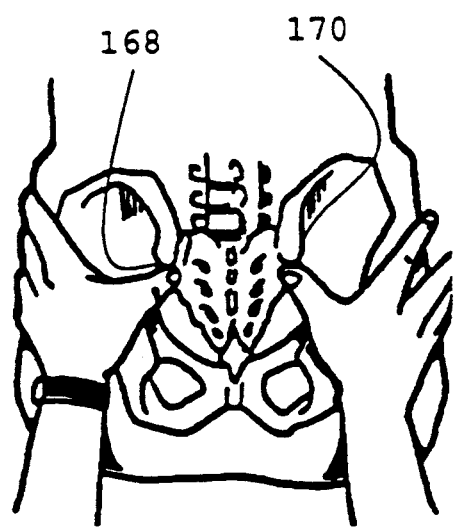
FIG. 20
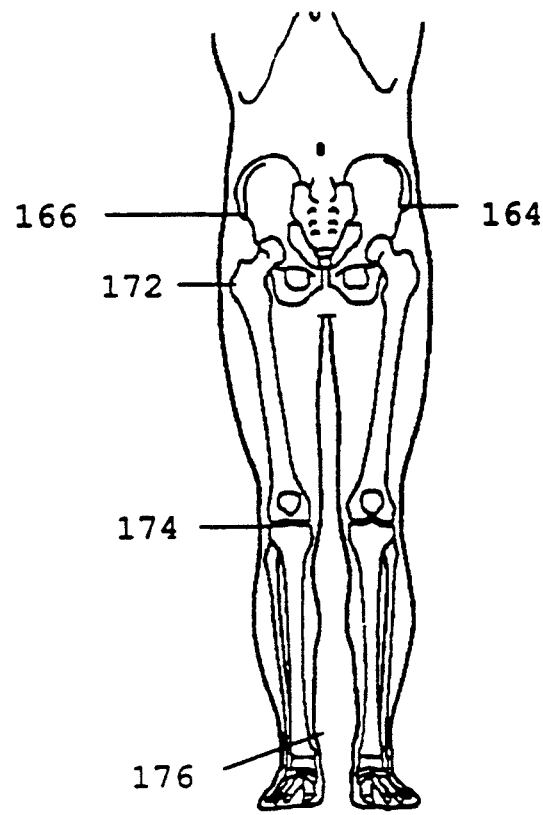
FIG. 21

BIOMECHANICAL MEASUREMENT TOOL

This invention relates to an apparatus for measurement of the human body. In particular, an apparatus and process is set forth in which measurement of the skeletal frame of the human body occurs through the skin and overlying flesh enabling diagnosis of skeletal related dysfunctions.

BACKGROUND OF THE INVENTION

Physical therapists and other health professionals such as physicians, chiropractors, and the like need to obtain precise and objective measurements of their patient's body skeletal structure. These precise measurements are necessary to help to determine the quality of function of a body by learning about its skeletal and related structure. Subtle deviations can exist in body structure that are of significance in the diagnosis of dysfunction that the eye of the practitioner itself might not see. Unless these subtle dysfunctions can be rapidly and repeatedly measured, therapists cannot monitor patient diagnosis and treatment progress objectively.

Present measurement techniques for the human body are not precise. Precision is necessary to increase accountability and objectivity of diagnosis and treatment. Further, precise measurements enable communication with third parties (other than therapist and patient). These third parties are most frequently insurance companies, lawyers, colleagues and other related medical professionals and medical groups all involved with the health care process and the vitally related reimbursement for treatment. When precision is lacking in describing dysfunction, questions as to the dysfunction and the treatment for the dysfunction frequently arise.

Further, present measurement techniques lacking accurate and quantitative measurement compound the difficulty of research.

Most health professionals operate under severe time limitations. There is a need for both improved accuracy and improved speed. Therefore, it is desired to have a precise measurement tool for skeletal measurement that operates through the skin and flesh that is easily handled by one person.

Body measurement tools have existed in the past. Generally, they consist of a pair of caliper arms attached in slidable and perpendicular relationship to a scaled straightedge. Thus the tool needs to be about as long as the distance that needs to be measured.

Unfortunately, with the use of such a tool, body landmarks that are poorly visible because they are obscured by a layer of skin and soft tissue need to be palpated before they can be measured. Loss of accuracy and time occurs in the period between the removal of the palpating fingers and the application of the measuring arms from the perpendicular straight edge to the area where measurement is of interest.

Another possibility and common practice in dealing with this type of landmarks is to mark the skin covering the landmarks with a pen after it has been palpated. Next, the measuring arms are applied to the pen marks on the skin. This introduces the possibility of additional inaccuracy, because the skin almost always moves relative to the landmarks.

Finally, and with linear arms protruding from a linear scale, each measurement requires multiple steps of unfastening, moving, refastening, and finally taking the measurement of the distance between the measured skeletal body parts.

Examples of the class of devices referred above to include Perrault U.S. Pat. No. 4,872,268 entitled SKELETON DEVICE and Phillips U.S. Pat. No. 4,201,226 entitled COMBINATION INSTRUMENT FOR TAKING BIOMECHANICAL MEASUREMENTS.

In another class of measurement devices, a floor mounted reference device in combination with calipers determines the angle of skeletal reference points by a combination of static measurement and trigonometry. Such calculation constitutes at a minimum an obstacle to rapid measurement.

An example of this type of measurement is described in "A Technique for Measuring Pelvic Tilt" by Sanders and Stavrakas, *Physical Therapy*, Volume 61, Number 1, January 1981.

SUMMARY OF THE INVENTION

A skeletal measurement device is disclosed in which concave arcuate calipers extend from a central housing containing a gear actuated dial scale. Upon expansion of the ends of the concave calipers away from one another in reaching and measuring skeletal points on a body therebetween, the gear actuated scale measures the distance between the caliper ends. Preferably, the arcuate calipers are extensible to at least first and second lengths. Accordingly, the connected gear actuated dial scale is provided with corresponding scales indicating the correspondingly changed distance of the extended arms. When the instrument is extended with its calipers measuring skeletal reference points, an attached inclinometer provides gravitational angular reference to the vertical. Dependent upon how the central housing must be disposed to enable the calipers to reach about the body being measured, this inclinometer is hinged along a hinge axis parallel to a line between the ends of the calipers to allow rapid measurement of distance and angle between skeletal points. Preferably, the measuring instrument is suspended by an adjustable cord from the neck of the measuring therapist to free his or her hands for palpation, data recording, safety of patient and movement of the measuring arms during rapid repeatable measurement. Provision is made for the attachment of palpation ends to the ends of the concave arcuate arms so that the skeletal points on a body can be palpated at the same time as the instrument is suspended around the therapist's neck and the measurements are read.

BRIEF DESCRIPTION OF THE DRAWINGS

FIG. 1 is a top view of the measuring device;

FIG. 2 is a enlarged cross sectional view along the section lines shown in FIG. 1 and 3 illustrating the spring lock mechanism used to arrest the tube of the arm within the outer tube;

FIG. 3 is a lateral view of one of the arms;

FIG. 4 is a lateral view of the pointed end of a tube of one of the arms;

FIG. 5 is a lateral view of the flat, ring shaped end of a tube of one of the arms;

FIG. 6 is an A/P (anterior/posterior) view of screw eye, washer and nut functioning as point of suspension on top of the device;

FIG. 7 is the front view of the caliper dial with centimeter and millimeter display;

FIG. 8 is a top view of the right arm, arrested in its short position;

FIG. 9 is a top view of the right arm, arrested in its extended position;

FIG. 18 left, lateral view of a patient during examination of pelvic alignment;

FIG. 19 same view of patient as in FIG. 19 with only the pelvis visible;

FIG. 20 posterior view of a patient during examination of pelvic alignment;

FIG. 21 anterior view of a patient during examination of pelvic alignment.

DESCRIPTION OF THE PREFERRED EMBODIMENT

Figure 10:
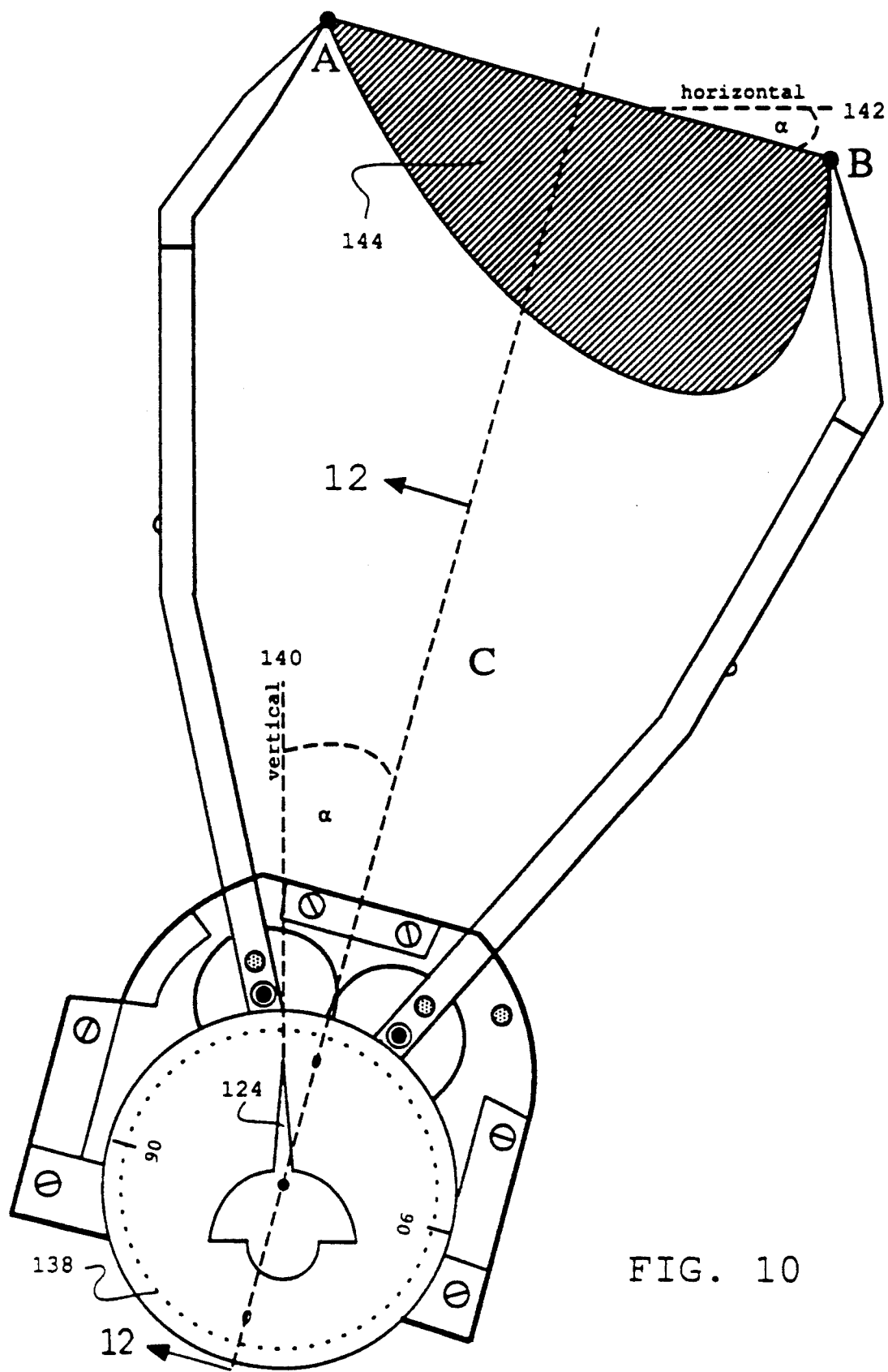
FIG. 10 is a bottom view of the device as it measures the inclination of a line through a body.

Two symmetrical concave and arcuate arms 22 are mounted to two coupled, equal and engaged cogs 80 and 82 by means of screws 68-74. Cog 80 swivels around axis 86. Cog 82 swivels around axis 90. Axis 86 and 90 are mounted between the top 50 and the bottom 52 of a housing. The housing consists of transparent plastic parts 42-52 (FIGS. 12 and 13) held together by screws 56-66. A third, smaller cog 84 is mounted on a third axis 88 and engages with one of the two larger cogs 80. The ratio of number of teeth is 1:8. All axes have a washer 108 on either side of their respective cog, preventing vertical movement of the cogs along their axis. The third axis 88 penetrates the top 50 of the housing. Stuck on top of this third axis 88 of the small cog 84 is a pointer 92. It is held by friction. When the arms 22 move apart through their entire range 100 of 90°, the pointer completes two complete revolutions clockwise on a dial 138 on top of the housing.

The dial FIG. 7 indicates the distance between the ends of the arms 22 in their extended position FIG. 9. It consists of two concentric circles showing centimeters and millimeters. The distance is read on the outer circle 110 during the first revolution of the pointer 92 and on the inner circle 112 during its second revolution.

A field 94 on the edge of the housing 50 indicates whether the pointer 92 is in its first or second revolution. A pointer 38 drawn on one of the arms 22 enters a field 94 marked on the edge of the housing 50 with the begin of the second revolution FIG. 12.

The dial 138 is protected by a plastic crystal 98. Both dial and crystal are screwed to the housing with screws 76 and 78. By unscrewing these screws, crystal and pointer can be removed and the dial 138 can be flipped around. The back side of the dial is structured in the same way as the front. The only difference is that it has been calibrated with the arms in their shortened position (FIG. 8). To shorten the arms, an inner, distal tube 26 is pushed all the way into an outer, proximal tube 24 of the arms 22. It is arrested in this position FIG. 8 by a spring lock mechanism (FIG. 2) as frequently used in crutches: The tube 26 contains a spring 34 that pushes a button 32 through a hole 30 in the outer tube 24 of the arms 22. When the arm is in its extended position FIG. 9, the button 32 arrests in a second, more distal hole 28 in the outer tube 24. To make it easier to find this second hole 28, a marked ring 36 on the tube 26 becomes visible when the arm is extended to the required length.

The device comes with two pairs of tubes 26. The first pair can be pulled out of the outer tube completely, so that it can be replaced with the second pair. The ends of the first pair of tubes 26 are pointed (FIG. 4). The ends of the second pair are flat and ring shaped (FIG. 5).

Fixed to the housing by means of a hinge 96, is an inclinometer 120. The pointer of the inclinometer has an counterweight 122 and a tip 124 portion. The pointer is suspended by two needles 126 and 128. The top of the inclinometer is covered by a plastic crystal 118. A degree scale 138 is printed on the inside of the bottom of the inclinometer. A thin magnetic layer 130 and 132 is glued to outside of the bottom of the inclinometer. When the magnetic layer 130 on the bottom of the inclinometer contacts a magnetic layer 134 glued to the bottom of the housing, the inclinometer is arrested in a position flat against the bottom of the housing FIG. 13. With a gentle pull the magnetic layers 130 and 134 can be separated and the inclinometer will swing freely with gravity FIG. 14. At the end of its range, the inclinometer arrests against the back of the housing FIG. 15, again by means of engagement of two magnetic layers 132 and 136.

Figures 16, 17:
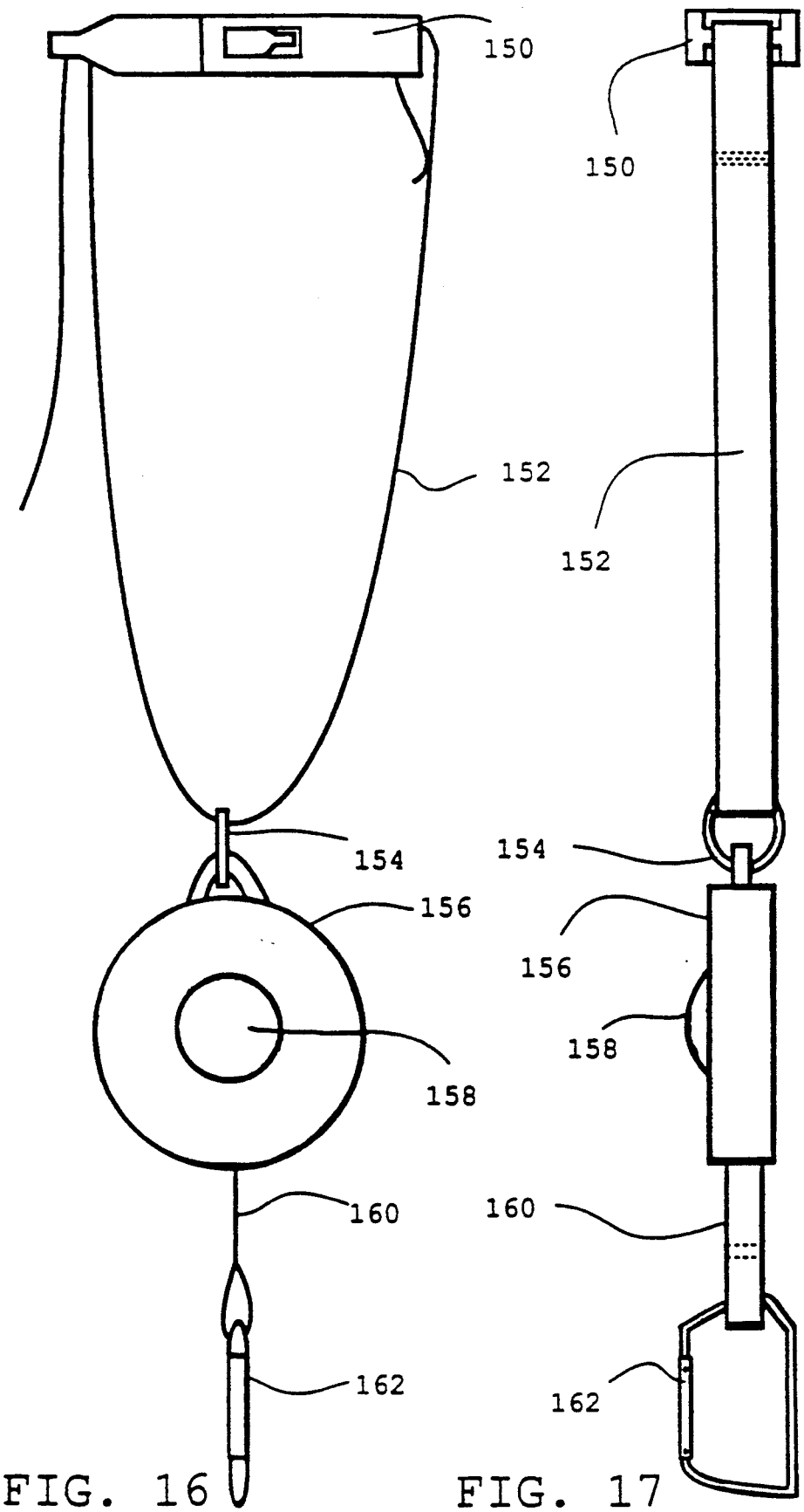
FIG. 16 is a front view of the suspension apparatus.
FIG. 17 is a lateral view of the suspension apparatus.

A screw eye 102 (FIG. 6) on the top of the device is used to attach it to a hook 162 of a suspension apparatus FIG. 16 and FIG. 17.

The suspension apparatus FIG. 16 and FIG. 17 consists of a buckle 150 with a loop of webbing 152 as it is frequently found in back packs. The buckle can be opened and closed. The length of the loop is adjustable in length and is worn around the examiner's neck. A ring 154 connects the webbing with a modified spring loaded tape measure 156. The tape measure has a button 158. When pushed, the button releases the spring inside the tape measure so that the tape 160 recoils. The modification of the tape measure consists in three features:

A ring on its top in which ring 154 engages. The end of the tape 160 forming a loop in which a hook 162 engages. The spring inside the tape measure being slightly stronger than the weight suspended.

Operation

Measurement of inclination is shown with respect to FIG. 10. Two symmetrical, curved arms are mounted to two coupled, equal and engaged gears in a housing. Thus the two arms move in a common plane and symmetrical with respect to a center line C through the housing. Fixed to the housing by means of a hinge, is an inclinometer 120. When the ends of the arms contact two points A +B on an incline of a degrees relative to the horizontal 142, housing and inclinometer dial incline a degrees as well. The pointer 122 and 124 of the inclinometer always tends to remain in vertical 140 alignment. Thus the dial will move relative to the pointer and indicate the angle.

Figure 13:
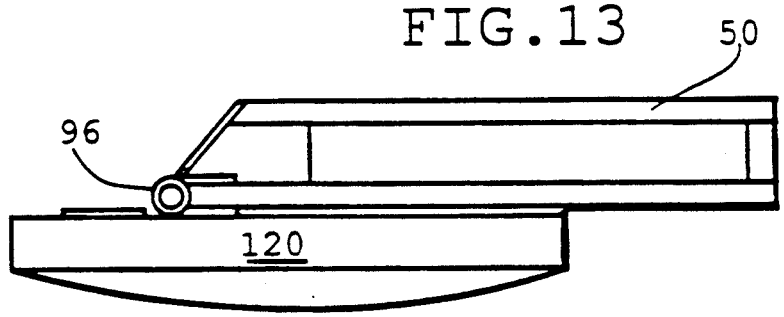
FIG. 13 is a schematic, lateral view of the device, with the inclinometer arrested against the bottom of the housing.
Figure 14:
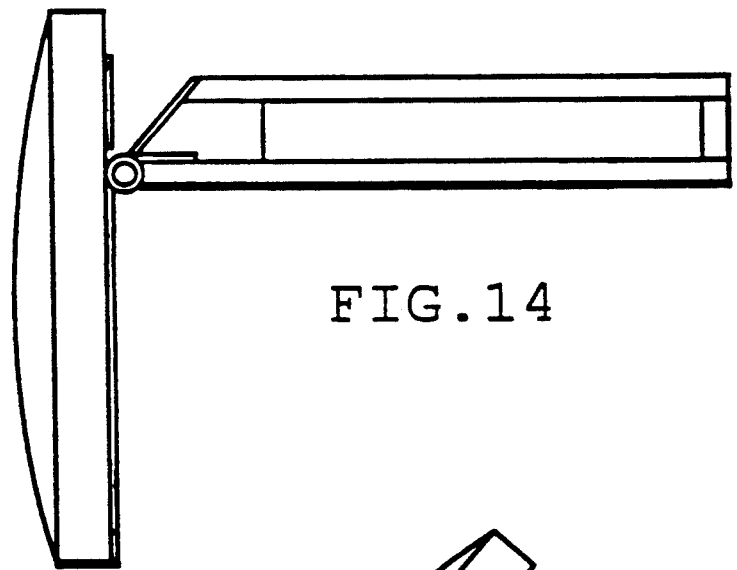
FIG. 14 is a schematic, lateral view of the device, with the inclinometer aligned with gravity.
Figure 15:
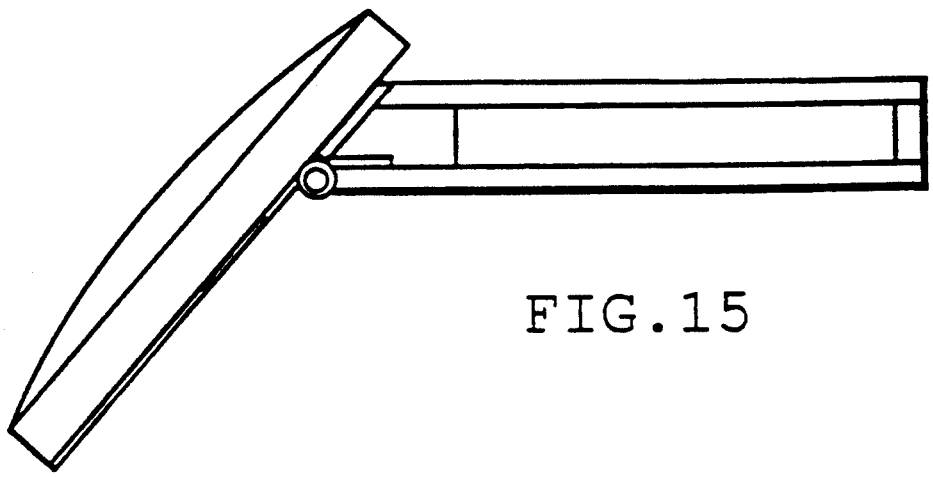
FIG. 15 is a schematic, lateral view of the device, with the inclinometer arrested against the back of the housing.

The inclinometer can be arrested against the bottom FIG. 13 or the back FIG. 15 of the housing or hinge freely with gravity FIG. 14 in the range between the two positions of arrest FIGS. 13 and 15. The examiner will chose the position in which the dial can viewed most conveniently.

Figure 11:
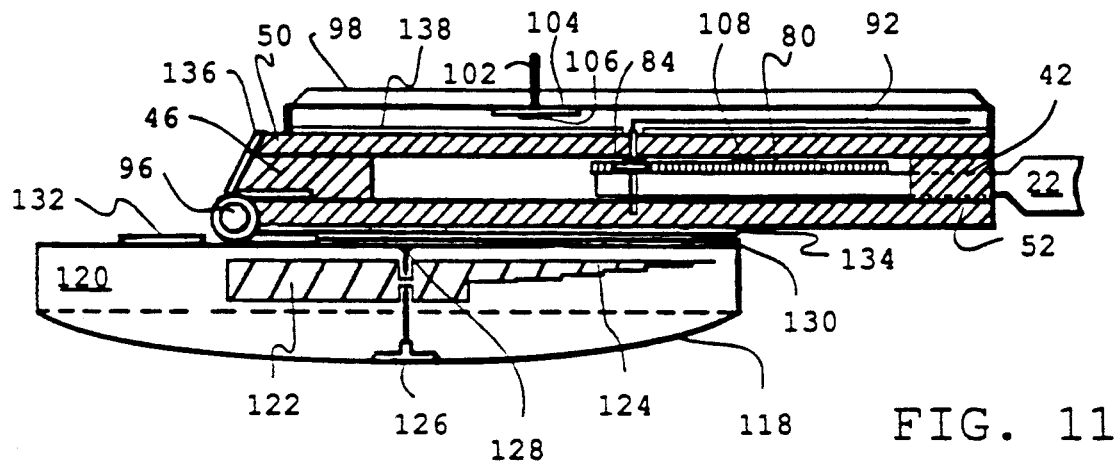
FIG. 11 is a lateral cross-sectional view along the center line "C" in FIG. 11 illustrating the left half of the body of the device.
Figure 12:
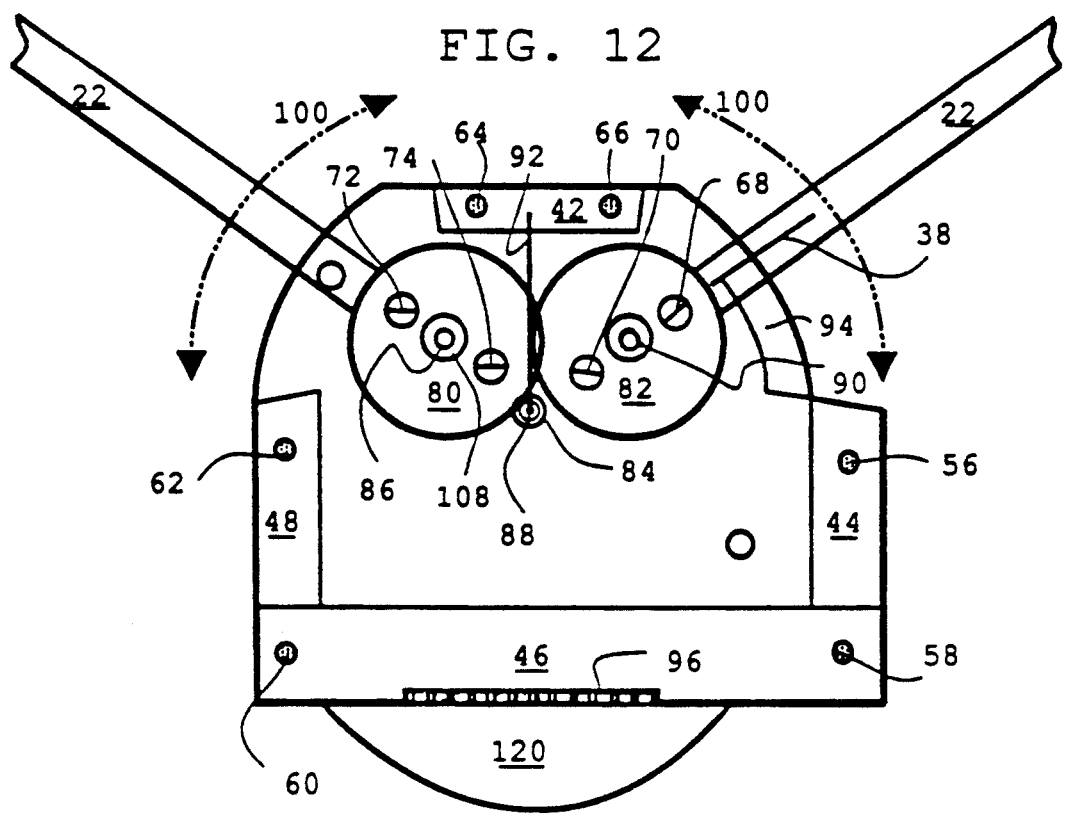
FIG. 12 is a top view of the device with truncated arms after unscrewing and removing the caliper dial and its crystal.

Measurement of distance is shown FIGS. 11 and 12. When the arms are moved apart to measure two points, the two equal and engaged cogs 80 and 82 will turn around their axis. Cog 80 drives a smaller cog 84. The smaller cog 84 turns with the axis 88 to which it is firmly glued. A pointer 92 is attached to the axis 88 of the smaller cog 84 and rotates clockwise on a dial 138 on top of the housing 50 of the device as the arms move apart. The dial indicates the distance between the points to be measured with extended arms FIG. 9.

If the examiner expects to use the device to measure shorter distances exclusively, he or she can shorten the arms (FIG. 8): After pushing the button 32 of the spring lock of the arms, the tube 26 can be slid into the outer tube 24.

Corresponding to the arms in their shortened position, is a scale on the backside of the caliper dial. To flip the caliper dial around, the screws 76 and 78, the crystal 98, and the pointer 92 are removed. After flipping the dial 138 around, pointer and crystal are reassembled.

Instead of contacting the points to be measured with the pointed ends of the arms, they can also be palpated directly through a flat ring. To do this, the spring locks FIG. 2 are released and the two tubes 26 with pointed ends are removed. Now a second set of tubes 26 with ring shaped ends FIG. 5 is inserted into the outer tube 24.

To free the hands of the examiner for palpation, the measuring device can be suspended around his or her neck. To do this the device is hooked into the hook 162 of a suspension apparatus FIGS. 16 and 17. The suspension apparatus includes a modified spring loaded tape measure 156. The spring inside the tape measure is slightly stronger than the weight of the measuring device. The tape unwinds with a gentle down pull on the device. Pushing the recoil button 158 will cause the tape to recoil and elevate the device, guided with one hand. Thus easy vertical mobility is provided.

When using the suspension apparatus the first time, the webbing band 152 is shortened as much as possible. This allows the suspended device to ride up high on the examiner. For following use, the suspension apparatus is donned and doffed by using the buckle 150 only.

The suspension apparatus is necessary only when two points are to be palpated directly through the ring-shaped ends FIG. 5 of the arms. If previously marked or easy visible points are contacted with the pointed ends of the arms, the device can be held with one hand while the other hand moves one of the arms. The other arm will move as well since both arms are coupled by the cogs 80 and 82 to which they attach.

Finally I want to describe a typical examination where the examiner palpates two points directly through the ring-shaped ends FIG. 5 of the arms:

The suspension apparatus is hung around the examiner's neck, by fastening the buckle 150 of the webbing loop 152. Then the hook 162 of the suspension apparatus is hooked into the screw eye 102 on top of the measuring device. Next, the device is pulled down to the desired level. The inclinometer is now arrested against the back of the housing (FIG. 15) so that it can be viewed easily from above. Finally the points to be measured are palpated trough the ring-shaped ends (FIG. 5) of the arms. Distance and inclination between the two points are displayed on caliper and inclinometer dial of the device.

Summary, Ramification, and Scope

The reader will understand that this invention can rapidly measure may skeletal features of the body. For example:

Instead of measuring ISJ (iliosacral joint) position, distance and inclination of a line between two points anywhere on any body, animate or inanimate, can be measured with my invention, Any definite measuring arm length is possible. The range of the caliper dial shown in FIG. 7 would vary according to the definite arm length chosen, The caliper dial could show angular movement "b" of one of the arms instead of centimeters and millimeters. This would allow for the use of arms of any definite length "L" without changing the caliper dial. With known distance between axis 86–90 "D", the measured distance could be calculated with the formula: $2*(L*\sin b)+D$ Different gear ratios, a different number of cogs and different means of transmission could be used as transmission between one of the main cogs 80 and 82 and the axis 88 to which the pointer 92 of the caliper dial attaches. This could result in a different amount of angular movement of the pointer 92 compared with the 720° = two complete revolutions in my preferred embodiment.

A digital inclinometer could be used instead of a mechanical inclinometer,

A digital display could be used instead of the caliper dial.

Thus the scope of the invention should be determined by the appended claims and their legal equivalents, rather than by the examples given.

What is claimed is:

1. A biomechanical measuring device enabling placement of the human digits of an examiner on body points of a patient being measured, said device comprising:
   a central housing;
   two measuring arms pivotally mounted to said housing at one end and extending away from said housing at a distal end, said arms mounted for pivotal movement with respect to a center line through said housing,
   means interconnecting said arms at said housing for indication of the distance between the distal ends of said arms during towards and away movement at said distal ends of said arms with respect to said housing; and,
   means at the ends of said arms distal of said housing for enabling palpation by the digits of said examiner at said arms on a measuring point at said body points to be measured to permit palpation insuring accurate measurement.

2. The biomechanical measuring device according to claim 1 and wherein:
   said two symmetrical measuring arms are concave and arcuate.

3. The biomechanical measuring device of claim 1 and wherein said symmetrical arms include:
   means for enabling adjustable changes in length of said arms.

4. The biomechanical measuring device of claim 3 and wherein said means for measuring the distance between the distal ends of said arms includes a pluarlity of scales for enabling the measurement of the distance between the distal ends of said arms when said arms are extended to said changes of length.

5. The biomechanical measuring device of claim 4 and said means at the ends of said arms for enabling palpation includes a flat ring shaped end that can be attached to the end of said arms and through which the points to be measured can be palpated directly.

6. The biomechanical measuring device of claim 1 and including:
   means for suspending said housing from a party utilizing said measuring device.

7. A process of measuring the skeletal anatomy of the human body of a patient utilizing biomechanical measuring device and palpation of points on said body by the digits of an examiner undertaking said measurement, comprising the steps of:
   providing a central housing;
   providing two measuring arms pivotally mounted to said housing at one end, said arms mounted for movement with respect to a center line through said housing,
   providing means operably connected between said arms and said housing for indicating the distance between the distal ends of said arm;
   opening said arms;
   placing said arms on skeletal features of a patient;
   measuring the distance between said skeletal features of said patient;
   placing means for palpating said skeletal features of said human body at the distal ends of said arms;
   palpating said skeletal features with the digits of said examiner at said points on said patients body being measured simultaneously with said measuring of said distance.

* * * * *

UNITED STATES PATENT AND TRADEMARK OFFICE
CERTIFICATE OF CORRECTION

PATENT : 5327907
DATED : JUL 12 1994
INVENTOR(S) : Peter Fisher

It is certified that error appears in the above-identified patent and that said Letters Patent is hereby corrected as shown below:

In the Drawings :

Sheet 3 of 4, Fig. 10, the numeral "12", indicating the cross section line, should be the numeral --11--.

Column 2, line 65, "Fig. 7 is the front view" should read -- Fig. 7 is a top view--

Signed and Sealed this

Eighteenth Day of October, 1994

Attest:

BRUCE LEHMAN

*Attesting Officer*  *Commissioner of Patents and Trademarks*